United States Patent
Williams et al.

(10) Patent No.: US 11,426,163 B2
(45) Date of Patent: Aug. 30, 2022

(54) UNIVERSAL LINEAR SURGICAL STAPLING BUTTRESS

(71) Applicant: Covidien LP, Mansfield, MA (US)

(72) Inventors: Justin Williams, Southbury, CT (US); Russell Pribanic, Roxbury, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 382 days.

(21) Appl. No.: 16/388,080

(22) Filed: Apr. 18, 2019

(65) Prior Publication Data

US 2019/0343522 A1     Nov. 14, 2019

Related U.S. Application Data

(60) Provisional application No. 62/668,851, filed on May 9, 2018, provisional application No. 62/668,858, filed on May 9, 2018.

(51) Int. Cl.
    *A61B 17/00*       (2006.01)
    *A61B 17/072*     (2006.01)
    *A61B 17/115*     (2006.01)

(52) U.S. Cl.
    CPC .... *A61B 17/07292* (2013.01); *A61B 17/1155* (2013.01); *A61B 2017/00424* (2013.01);
(Continued)

(58) Field of Classification Search
    CPC ........ A61B 17/07292; A61B 17/07207; A61B 2017/07257; A61B 2017/07271
See application file for complete search history.

(56) References Cited

U.S. PATENT DOCUMENTS 3,054,406 A     9/1962    Usher
3,079,606 A     3/1963    Bobrov et al.
(Continued)

FOREIGN PATENT DOCUMENTS

CA       2282761 A1    9/1998
DE       1602563 U     3/1950
(Continued)

OTHER PUBLICATIONS

European Office Action corresponding to EP 14 17 2681.0 dated May 13, 2016.
(Continued)

*Primary Examiner* — Chelsea E Stinson
(74) *Attorney, Agent, or Firm* — Carter, DeLuca & Farrell LLP

(57) ABSTRACT

A surgical buttress carrier assembly includes a buttress carrier and a buttress material. The buttress carrier has a body, a distal end, and lateral sides; the carrier has at least one distally extending post at the distal end, at least one first laterally extending post at a first lateral side, and at least one second laterally extending post at a second lateral side. The buttress carrier has an inner edge adjacent the distal end, and a proximally extending hook extending from the inner edge. The buttress material has an elongate shape, a distal end, and a first lateral side and a second lateral side; the buttress material has at least one opening at the distal end, at least one first side opening adjacent the buttress first lateral side, and at least one second side opening adjacent the buttress second lateral side.

20 Claims, 12 Drawing Sheets

(52) U.S. Cl.
CPC .............. *A61B 2017/00477* (2013.01); *A61B 2017/07257* (2013.01); *A61B 2017/07271* (2013.01)

(56) References Cited

U.S. PATENT DOCUMENTS

| | | |
|---|---|---|
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,137,198 A | 8/1992 | Nobis et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,865,361 A | 2/1999 | Milliman et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Di et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,202,914 B1 | 3/2001 | Geiste et al. |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |

(56) References Cited

U.S. PATENT DOCUMENTS

| | | |
|---|---|---|
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,256,656 B2 | 9/2012 | Milliman et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |

(56) References Cited

U.S. PATENT DOCUMENTS

| | | |
|---|---|---|
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0091397 A1 | 7/2002 | Chen |
| 2002/0151911 A1 | 10/2002 | Gabbay |
| 2002/0165562 A1 | 11/2002 | Grant et al. |
| 2002/0165563 A1 | 11/2002 | Grant et al. |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0004407 A1* | 1/2006 | Hiles .................. A61B 17/0644 606/215 |
| 2006/0008505 A1 | 1/2006 | Brandon |

(56) References Cited

U.S. PATENT DOCUMENTS

| | | |
|---|---|---|
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0076510 A1 | 3/2009 | Bell et al. |
| 2009/0076528 A1 | 3/2009 | Sgro |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0065606 A1 | 3/2010 | Stopek |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0145767 A1 | 6/2012 | Shah et al. |
| 2012/0197272 A1 | 8/2012 | Gray et al. |
| 2012/0228360 A1 | 9/2012 | Hodgkinson et al. |
| 2012/0234900 A1 | 9/2012 | Swayze |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1* | 8/2015 | Racenet ........... A61B 17/07292 227/175.1 |
| 2015/0327864 A1 | 11/2015 | Hodgkinson et al. |
| 2015/0351758 A1* | 12/2015 | Shelton, IV ..... A61B 17/00491 606/219 |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0345976 A1* | 12/2016 | Gonzalez ......... A61B 17/07207 |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0303952 A1* | 10/2017 | Nativ ............... A61B 17/07207 |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 07124166 | 5/1995 |
| JP | 2000166933 A | 6/2000 |
| JP | 2002202213 A | 7/2002 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.

(56) References Cited

OTHER PUBLICATIONS

European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8//6.2 dated Sep. 12, 2016.
Japanese Office Action corresponding to JP 2013-000321 dated Sep. 13, 2016.
Chinese Second Office Action corresponding to ON 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2 017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Australian Examination Report No. 1 corresponding to AU 2014200793 dated Sep. 2, 2017.
Extended European Search Report corresponding to EP 17 17 8528.0 dated Oct. 13, 2 017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11,2 017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2 018.
Extended European Search Report corresponding to Patent Application EP 18192317.8 dated Dec. 20, 2018.
Extended European Search Report corresponding to Patent Application EP 18190154.7 dated Feb. 4, 2019.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008 (5 pp).
European Search Report corresponding to EP 08 25 1989.3, completed Mar. 11, 2010 and dated Mar. 24, 2010; (6 pp).

(56) References Cited

OTHER PUBLICATIONS

European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and mailed Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and daed Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 182911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Extended European Search Report corresponding to EP 14 16 9739 1, completed Aug. 19, 2014 and dated Aug. 29, 2014; (7 pp).
Extended European Search Report corresponding to EP 14 15 7997 9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated August 6,2 015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.

(56) References Cited

OTHER PUBLICATIONS

Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
Partial European Search Report dated Oct. 4, 2019 corresponding to counterpart Patent Application EP 19173233.8.
Extended European Search Report dated Mar. 3, 2020 corresponding to counterpart Patent Application EP 19173233.8.
Extended European Search Report dated Dec. 15, 2020 corresponding to counterpart Patent Application EP 20207294.8.

* cited by examiner

UNIVERSAL LINEAR SURGICAL STAPLING BUTTRESS

CROSS-REFERENCE TO RELATED APPLICATIONS

This application claims the benefit of, and priority to, U.S. Provisional Patent Application No. 62/668,851, filed May 9, 2018, and U.S. Provisional Patent Appl. No. 62/668,858, filed May 9, 2018, the entire contents of each of which being hereby incorporated herein by reference.

TECHNICAL FIELD

This application relates to a surgical buttress assembly, and to surgical stapling apparatus and buttress assemblies, and to methods of assembling a buttress to a surgical stapler, more particularly, to an endoscopic surgical buttress, endoscopic surgical stapler, and assemblies and kits.

BACKGROUND

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

Although the present disclosure includes, but is not limited to use with endoscopic surgery, endoscopic surgery is a great advance, reducing the invasiveness of surgical procedures, and improving recovery time. Generally, endoscopic surgery involves incising through body walls for example, viewing and/or operating on the ovaries, uterus, gall bladder, bowels, kidneys, appendix, etc. There are many common endoscopic surgical procedures, including as examples arthroscopy, laparoscopy (pelviscopy), gastroentroscopy and laryngobronchoscopy. Typically, trocars are utilized for creating the incisions through which the endoscopic surgery is performed, and are used with cannula assemblies for creating access and maintaining pneumoperitoneum in the abdominal space. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

In many surgical procedures, including those involved in open and endoscopic surgery, it is often necessary to staple tissue. It is especially challenging during endoscopic surgery because of the small openings through which the stapling of tissues must be accomplished. Instruments for this purpose can include two elongated members which are respectively used to capture or clamp tissue. Surgical devices wherein tissue is first grasped or clamped between opposing jaw structure and then joined by surgical fasteners are well known in the art. Typically, one of the members carries a fastener cartridge which houses a plurality of staples arranged in at least two lateral rows while the other member has an anvil that defines a surface for forming the staple legs as the staples are driven from the staple cartridge. The fasteners are typically in the form of surgical staples but two part polymeric fasteners can also be utilized. Generally, the stapling operation is effected by cam bars or wedges that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. Nos. 3,079,606 and 3,490,675.

A later stapler disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. U.S. Surgical, the assignee of the present application, has manufactured and marketed endoscopic stapling instruments for several years. Examples of such instruments include the Multifire ENDO GIA™ 30 and ENDO GIA™ endoscopic surgical instruments. Other examples of such staplers are disclosed in U.S. Pat. Nos. 4,429,695 and 5,065,929.

Certain endoscopic surgical staplers have stapler jaws that are integral to the stapler handle, and a surgical stapling cartridge is removable and replaceable for continued use on the same patient. In other configurations, a surgical stapling reload has stapler jaws and a body that can be attached to a stapling handle. The reload can be used, removed and replaced with a reload having a new set of staples ready to be fired. Reloads having stapler buttress material pre-attached to the jaws have been developed as Endo GIA™ Reinforced Reloads.

However, surgical stapling buttresses can be provided separately from the stapling device. Buttresses can be used with circular surgical staplers, linear surgical staplers intended for open surgery, endoscopic instruments, and other kinds of staplers and instruments.

Surgical buttress material may be used in combination with these instruments as reinforcement to staple lines to further promote proper staple formation while reducing twisting/malformation caused by any misalignment or unusual or non-uniform tissue. Surgical buttresses can provide support to weakened tissue, or help to address differences in the thickness of tissues. These instruments have provided significant clinical benefits. Nonetheless, improvements are possible, for example, by reducing the complexity of manufacture and/or application, or by expanding the range of applications for the use of the buttress material.

A surgical buttress for use with a surgical stapling apparatus having jaws is disclosed in U.S. Pat. No. 8,348,130 to Shah et al., the entire disclosure of which is hereby incorporated by reference herein. The buttress disclosed therein has a first body portion and a second body portion. The first body portion can be applied to the first jaw, which can be a staple cartridge of the stapling apparatus, and the second body portion can be applied to the second jaw, which can be a stapling anvil. It is also disclosed that the first body portion of the buttress can be attached to a replacement staple cartridge. When the staple cartridge is attached to the surgical stapling apparatus, the second body portion can be attached to the anvil.

Improvements in surgical buttresses are desired to permit re-use of certain instruments, or portion thereof, and to allow surgical stapling instruments and other apparatus to be configured in various ways.

SUMMARY

In an aspect of the present disclosure, a surgical buttress carrier assembly comprises a buttress carrier and a buttress material. The buttress carrier has a body, a distal end, and lateral sides; the carrier has at least one distally extending post at the distal end, at least one first laterally extending post at a first lateral side, and at least one second laterally extending post at a second lateral side. The first lateral side is opposite the second lateral side. The buttress carrier has an inner edge adjacent the distal end, and a proximally extending hook extending from the inner edge. The buttress material has an elongate shape, a distal end, and a first lateral side and a second lateral side; the buttress material has at least one opening at the distal end, at least one first side opening adjacent the buttress first lateral side, and at least one second side opening adjacent the buttress second lateral side. The at least one distal opening receives the at least one distally extending post, the at least one first side opening receives the at least one first laterally extending post, and the at least one second side opening receives the at least one second laterally extending post.

In the surgical buttress carrier assembly, the at least one distally extending post can comprise a first distal post and a second distal post, the at least one first laterally extending post can comprise a first side post, and a second side post, and the at least one second laterally extending post can comprise a third side post, and a forth side post. In other embodiments, there are four posts on one lateral side, four posts on the other lateral side of the carrier, and two posts on the distal end, the buttress material having corresponding openings.

In an embodiment, the surgical buttress carrier assembly has a buttress material with a first distal opening and a second distal opening, a first side opening and a second side opening, and a third side opening and a forth side opening.

The buttress carrier may extend from a proximal end of the buttress material to the distal end of the buttress material. The buttress carrier can have a shape corresponding to the shape of at least one of the anvil stapler jaw and the cartridge stapler jaw.

In a further aspect, a staple cartridge assembly comprises a staple cartridge body housing a plurality of staples in staple retaining slots, the staple cartridge body housing staple pushers, the staple cartridge body defining a knife slot. The assembly includes a buttress carrier having a body, a distal end, and lateral sides, the carrier having at least one distally extending post at the distal end, at least one first laterally extending post at a first lateral side, and at least one second laterally extending post at a second lateral side, wherein the first lateral side is opposite the second lateral side, the buttress carrier having an inner edge adjacent the distal end, and a proximally extending hook extending from the inner edge, the hook engaging the knife slot of the staple cartridge body. The assembly has a buttress material having an elongate shape, a distal end, and a first lateral side and a second lateral side, the buttress material having at least one distal opening at the distal end, at least one first side opening adjacent the buttress first lateral side, and at least one second side opening adjacent the buttress second lateral side, the at least one distal opening receiving the at least one distally extending post, the at least one first side opening receiving the at least one first laterally extending post, and the at least one second side opening receiving the at least one second laterally extending post.

The at least one distally extending post can comprise a first distal post and a second distal post, the at least one first laterally extending post can comprise a first side post, and a second side post, and the at least one second laterally extending post can comprise a third side post, and a forth side post.

The at least one opening can comprise a first distal opening and a second distal opening, the at least one first side opening can comprise a first side opening and a second side opening, and the at least one second side opening can comprise a third side opening and a forth side opening. In other embodiments, the carrier can have two distally extending posts, four laterally extending posts on the first lateral side and four laterally extending posts on the second lateral side, and the buttress material has a corresponding set of openings.

The buttress carrier can extend from a proximal end of the buttress material to the distal end of the buttress material. The buttress carrier can have a shape corresponding to the shape of the cartridge stapler jaw, or the anvil jaw.

In another aspect, a method of using a surgical stapler comprises grasping a first buttress carrier assembly, the first buttress carrier assembly having a buttress material, sliding the first buttress carrier assembly onto an anvil of the surgical stapler in a proximal direction, firing staples from a staple cartridge of the endoscopic surgical stapler; dividing the buttress material longitudinally while dividing tissue; grasping a first portion of the buttress material and grasping a second portion of the buttress material and laterally moving the first portion and second portion away from each other and away from the anvil, and removing the buttress carrier and surgical stapler from the surgical site.

The method can include sliding a second buttress carrier assembly onto a staple cartridge jaw of the surgical stapler.

In another aspect, a method of reloading a surgical stapling instrument comprises providing a staple cartridge assembly having a buttress material pre-loaded thereon, providing a buttress carrier assembly having a carrier and a buttress material, engaging the staple cartridge assembly with a first jaw of the surgical stapling instrument, and engaging the buttress carrier assembly with a second jaw of the surgical stapling instrument, the second jaw having a stapling anvil.

In the method, the buttress material can define openings and the carrier can have posts, the posts being disposed in the openings to retain the buttress material on the carrier.

In a further aspect, a surgical buttress carrier assembly comprises a buttress carrier and a buttress material. The buttress carrier has a body and lateral sides, the carrier having a plurality of distally extending arms on each of the lateral sides. The lateral sides include a first lateral side and a second lateral side, the first lateral side being opposite the second lateral side. The buttress material has an elongate shape, a distal end, and a first lateral side and a second lateral side, the buttress material having a plurality of openings at the buttress first lateral side and buttress second lateral side. The plurality of openings correspond to the plurality of distally extending arms. The buttress carrier assembly has an elongate member extending proximally from the buttress carrier, the buttress carrier being separated from the buttress material when the elongate member is pulled.

The elongate member can be integral with the buttress material, or separate and attached to the buttress material. The elongate member can be a suture. In an example, there are at least three distally extending arms on the first lateral side and at least three distally extending arms on the second lateral side. In another example, there are at least three openings on the buttress first lateral side and at least three openings on the buttress second lateral side.

The buttress carrier can extend from a proximal end of the buttress material to the distal end of the buttress material. The buttress carrier can flexibly conform to the shape of a selected one of the anvil stapler jaw and the cartridge stapler jaw.

In another aspect, a surgical buttress component comprises an elongate member, a folded portion, and a buttress portion, the folded portion being folded over the buttress portion. The component forms an elongate tubular shape for the reception of a selected one of the anvil stapler jaw and the cartridge stapler jaw, the component further comprising a feature selected from the group consisting of a perforation, an elongate opening and a line of weakness separating the buttress portion from the folded portion.

The buttress component can be formed from a buttress material. The buttress component can be formed from a material selected from the group consisting of a woven, a non-woven, and a mesh. The buttress material can be formed from a bio-absorbable polymer. The elongate member can be long enough to extend the length of an endoscopic shaft of an endoscopic stapler, and can be made from the same material as the buttress material. The elongate member can be accessible outside the patient's body.

The elongate member can be a suture attached to the folded portion. The folded portion can be formed from more than one section of material. The folded portion can be made from the same material as the buttress material. Furthermore, the folded portion can be made from the same sheet of material as the buttress portion. The folded portion can be welded to form the tubular shape, and/or the folded portion is attached to the buttress material.

In a further aspect, a method of forming a surgical stapling buttress component includes providing a buttress material, forming at least one feature selected from the group consisting of a perforation, an opening, and a line of weakness, the at least one feature defining a buttress portion and a folded portion, forming an elongate member extending away from the buttress portion and the folded portion, the elongate member being formed from the buttress material, folding the folded portion over the buttress portion, and attaching the folded portion to itself or to the buttress portion to form a tubular shape.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

Figure 1:
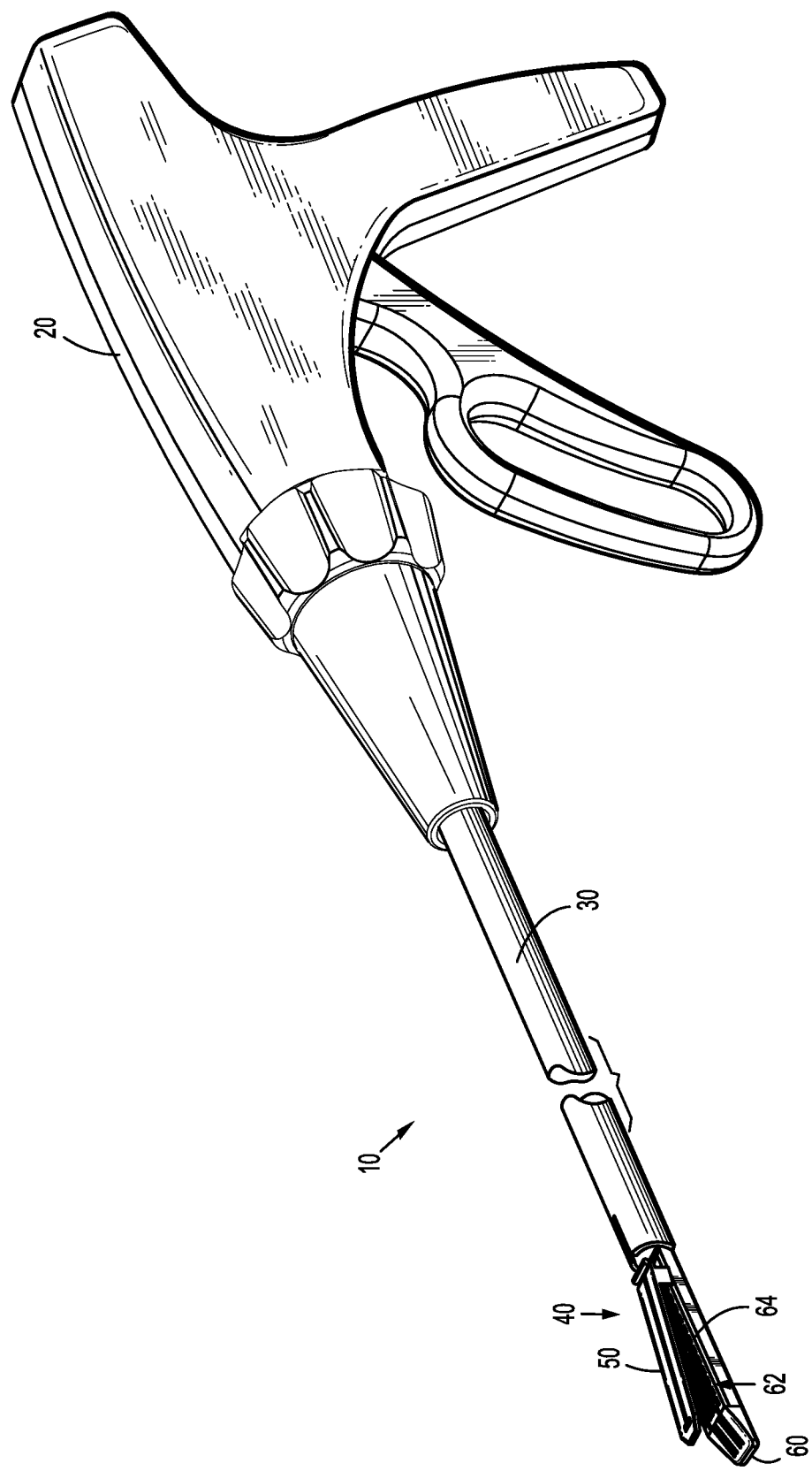
FIG. 1 is a perspective view of an exemplary endoscopic surgical stapler according to the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is farther from the user. In the following description, well-known functions or constructions are not described in detail to avoid obscuring the present disclosure in unnecessary detail.

Figure 2:
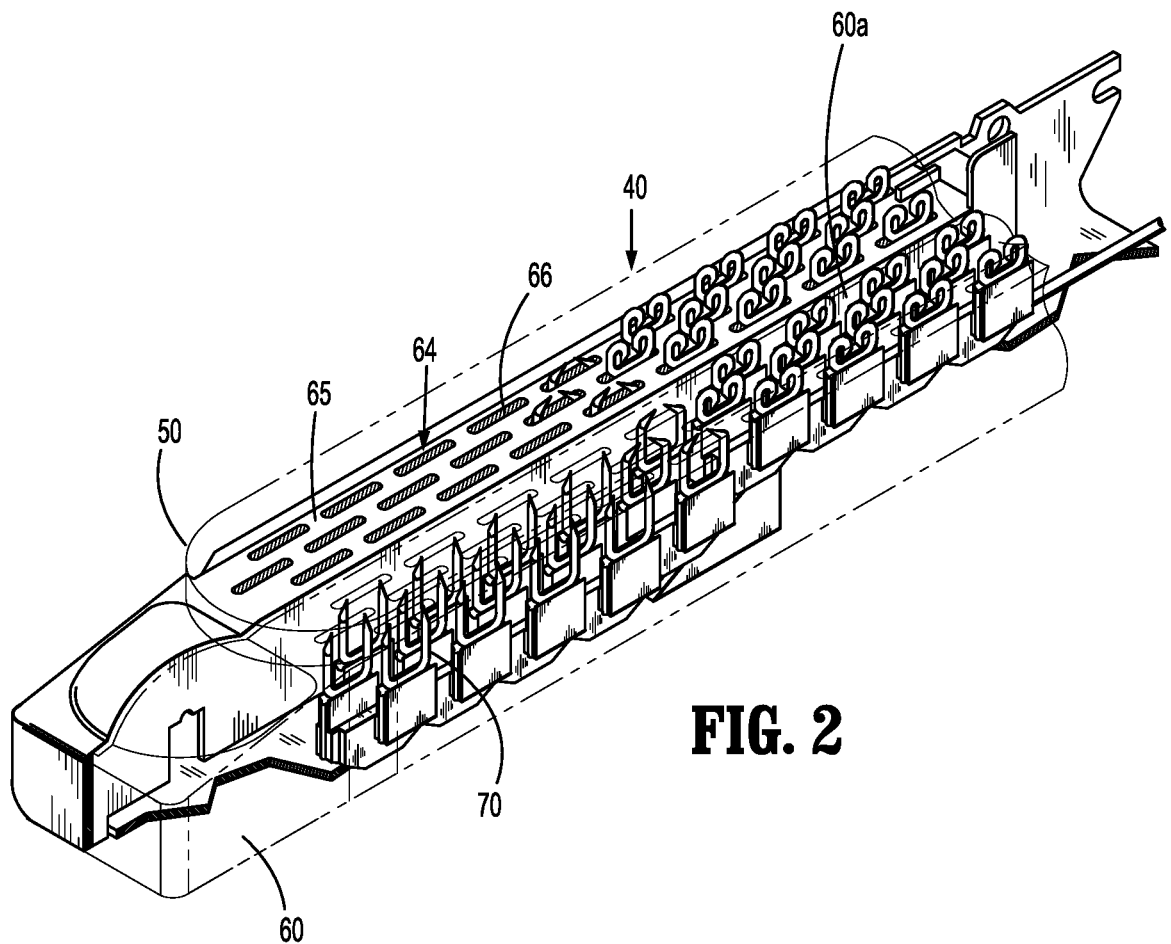
FIG. 2 is an enlarged perspective view illustrating an exemplary end effector of the surgical stapler of FIG. 1 during a fastener applying operation as fasteners are being sequentially fired.
Figure 2A:
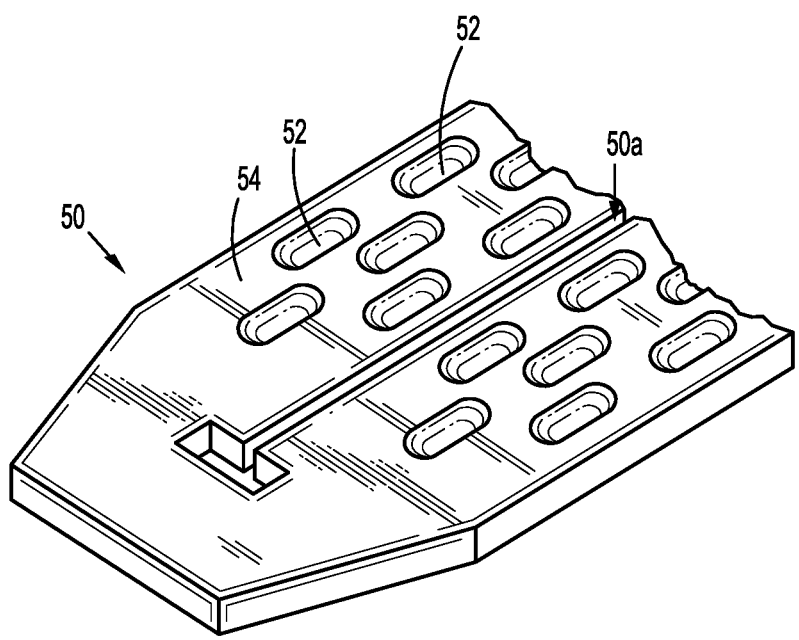
FIG. 2A is a bottom perspective view of a distal portion of an exemplary anvil of the end effector shown in FIG. 2.

Referring now to the drawings, in which like reference numerals identify identical or substantially similar parts throughout the several views, FIG. 1 illustrates a surgical stapling apparatus 10. In accordance with the present disclosure, a surgical stapling apparatus 10 includes a housing 20 or handle and an elongate member 30 extending from the housing 20. An end effector 40 is disposed on one end of the elongate member 30. The end effector 40 includes first and second jaws 50, 60. The first jaw 50 is the form of an anvil assembly and the second jaw 60 is receives a staple cartridge 62 (which may or may not be removable and replaceable). With reference to FIGS. 1 and 2, the staple cartridge 62 includes a cartridge housing 64 defining a longitudinal axis and including a tissue contact surface 65 having a plurality of rows of staple retaining slots (also referred to herein as stapler slots and fastener slots) 66 formed therein that house a plurality of fasteners or staples 70. As best shown in FIG. 2A, the plurality of staples 70 may be formed into a closed shape by fastener pockets 52 defined in a tissue contacting surface 54 of the first jaw 50 (anvil assembly).

The staple cartridge 62 defines linear rows of staple retaining slots 66 on either side of a knife slot 60a. The anvil has corresponding linear rows of staple pockets/recesses, on either side of a knife slot 50a. (FIG. 2A). During firing of the staples 70, a staple firing mechanism moves distally through the staple cartridge and anvil, ejecting the staples from the slots, and driving them into the anvil pockets. The staple firing mechanism moves distally, interacting with staple pushers, and the pushers drive the staples out of the slots 66. The staples 70 are shown in FIG. 2 supported by the pushers. The anvil pockets 52 are specially shaped to bend legs of the staple into a closed, B-shaped form. The anvil 50 has a rear surface 51 opposite the tissue contacting surface 54, and the jaw 60 has a rear surface 61 opposite the tissue contacting surface 65 of the staple cartridge. See an example of an endoscopic stapler in U.S. Pat. No. 8,256,656 to Milliman et al., the entire disclosure of which is hereby incorporated by reference herein.

Figure 3:
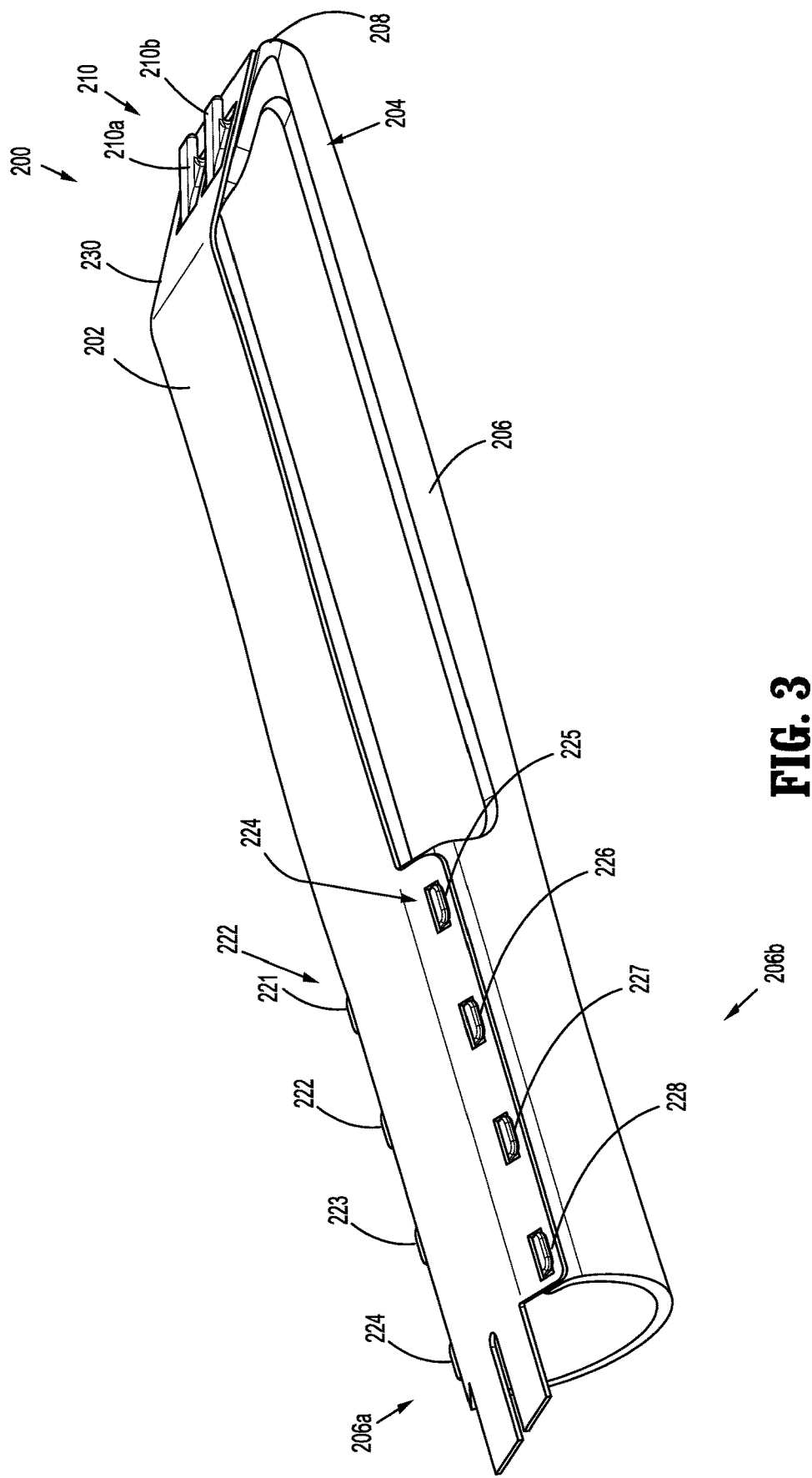
FIG. 3 is a perspective view of a buttress carrier assembly according to certain aspects of the present disclosure.

As best shown in FIG. 3, a surgical buttress material 202 is attached to a buttress carrier 204 to form a buttress carrier assembly 200. (As used herein, "buttress" includes a pledget, gasket, buttress, or staple line reinforcement structure). The buttress carrier 204 has a body 206 with a distal end 208, and at least one post 210 extending distally from the body 206. The body 206 can be formed from a thin sheet of plastic or polymeric material and the post 210 can be integrally formed with the body. In the example shown, two distal posts 210a and 210b are disposed on the buttress carrier body.

The buttress carrier body 206 can be molded, cut, extruded, or otherwise formed from the plastic/polymeric material. The material for the carrier body may also be a thin sheet metal or foil. The carrier body defines a proximally-facing hook 214 on an inside edge 212 of the distal end 208 of the carrier body (best seen in FIG. 8). The hook 214 snaps into or otherwise engages the knife groove/slot to retain the sleeve on the staple cartridge or anvil after firing. The engagement of the hook 214 should be secure enough that the carrier body 206 does not remain at the surgical site after the firing of the staples, and is removed with the surgical stapler.

The body 206 has two lateral sides 206a and 206b and, at least one post 220 on each of the sides. A first side 206a of the body has at least a first side post 222, and the second side 206b has at least a second side post 224. In the example shown, the first side 206a has a first 221, second 222, third 223, and a forth 224 post extending laterally and away from the body 206, whereas the second side 206b has a fifth 225, sixth 226, seventh 227, and eighth 228 post extending laterally and away from the body. The first, second, third, and forth post extend in a direction opposite the direction that fifth, sixth, seventh, and eighth posts extend. The posts can have a slight upward (or downward) slant, slanting away from the buttress material, to further help retain the buttress material on the carrier 204.

In embodiments, at least a portion of the surgical buttress 202 may be made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In embodiments, at least a portion of the surgical buttress 110 may be made from non-biodegradable materials selected from the following group: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes.

The buttress material may be a non-woven material formed by melt-blown or melt-spun methods, a mesh material, a braid material, and/or a molded or extruded sheet. The buttress material 202 has a distal end 230 that defines at least one opening 232 corresponding to the distal post or posts 210 in the buttress carrier 204. In the example shown, the buttress material has a distal end defining two openings: a first distal opening 230a to receive the first distal post 210a and a second distal opening 230b to receive the second distal post 210b. In alternative examples, the posts can be used to puncture the buttress material and form the openings. However, the posts are preferably atraumatic to tissue and have a rectangular shape with rounded corners (although other shapes can be used).

The buttress material 202 has lateral side openings 240 to correspond to the side posts 220. The buttress material 202 defines first side openings 242 adjacent one lateral edge 245 of the buttress material 202 and second side openings 244 adjacent the other lateral edge 246 of the buttress material 202, to correspond to the posts. In the example shown, the buttress material 202 has a first 251, second 252, third 253, and a forth 254 opening adjacent one lateral edge 245, and a fifth 255, sixth 256, seventh 257, and eighth 258 openings adjacent the other lateral edge 246 of the buttress material. As discussed further below, the buttress material 202 can include perforations or weakened areas adjacent the lateral portions of the buttress that have the openings, and/or adjacent the distal portion of the buttress material that has the opening or openings. The perforations and/or weakened areas can facilitate in the removal of any excess material.

The surgical buttress is provided and/or sold separately as a surgical buttress carrier assembly 200 including the buttress material 202 and buttress carrier 204. In other examples, the surgical buttress and buttress carrier are provided and/or sold separately and assembled by the user.

The surgical stapling instrument, whether of the type that has a replaceable staple cartridge, or a replaceable stapling reload, can be packaged with a surgical buttress disposed on the tissue contacting face of the staple cartridge, and a buttress disposed on the tissue contacting face of the anvil (see FIG. 4), and retained thereon by the buttress carrier 204 that extends on the opposite surface 61 of the respective cartridge 62 or the opposite or rear surface 51 of the anvil 50. Accordingly, in such an example, the buttress carrier is used to stabilize the buttress material during shipping, etc.

Advantageously, a separately sold buttress carrier assembly 200 can be applied to any endoscopic stapler anvil or cartridge. The buttress carrier assembly 200 having a surgical buttress material 202 attached to a buttress carrier 204, is removed from its package. The user grasps the buttress carrier 204 and manipulates the assembly 200 to the surgical stapling instrument 300. It may be useful for the buttress carrier 204 to be slightly more rigid than the buttress material 202 to ease manipulation of the assembly. Furthermore, the buttress carrier 204 can include a tab, handle or other feature, or textured surfaces, for ease of grasping and manipulation.

The assembly 200 is slid onto the stapler jaw. The elongate shape of the assembly 200, corresponding to the stapler jaw, facilitates the ease of application. The buttress material 202 is naturally disposed adjacent the tissue contacting surface of the staple cartridge or anvil. The shape of the buttress carrier 204 can be suggestive of the correct application of the assembly, as it corresponds to the curved shape of the rear of the jaw. The hook 214 can be omitted from the carrier 204, and in that case, the assembly 200 is retained on the jaw by frictional forces between the carrier 204 and the jaw, and between the buttress material 202 and the jaw. Alternatively, the assembly 200 can be attached to the instrument jaws using adhesive, tied on using sutures, or by some other method.

Once assemblies 200 are applied to each jaw, as it is typical to apply buttress to both the staple cartridge jaw 304 and the anvil jaw 306 when using surgical buttress, the stapling instrument 300 is introduced to the surgical site through a trocar or other access device. The stapler 300 is operated as normal, and staples are fired into tissue and the tissue is transected. As the tissue is transected, the buttress material 202 is divided as well, into a first portion 202a and a second portion 202b. In the example shown in FIG. 5, the divided buttress material 202 includes a distal tab 260 that remains attached to the tissue. This distal tab 260 can remain in the patient's body, or it can be removed using a scalpel or surgical shears. In any of the examples disclosed herein, the buttress material 202 can include perforations adjacent the portions of the buttress that have the openings, so that excess material can be removed.

Figure 5:
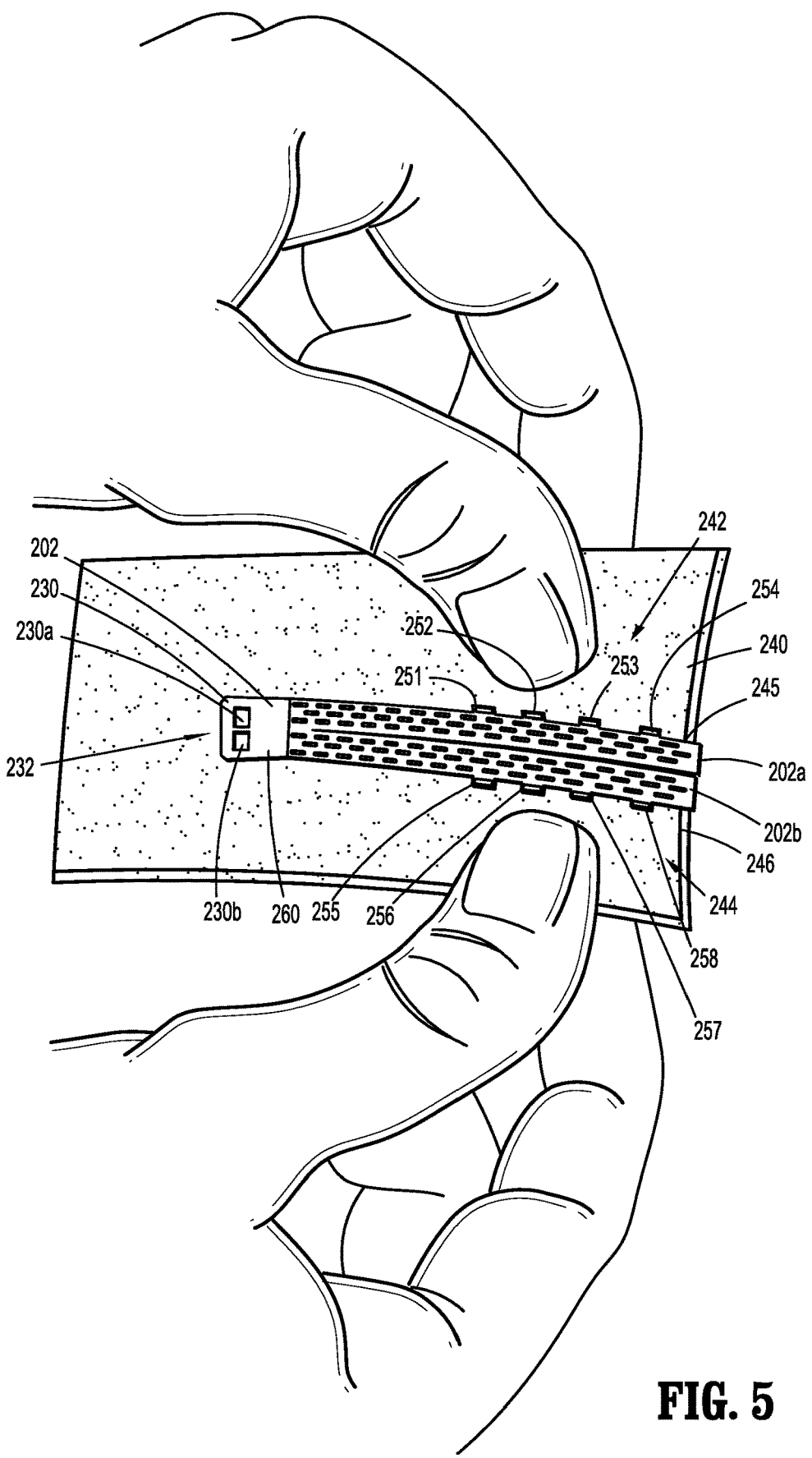
FIG. 5 is a top plan view of the buttress material attached to foam material by linear rows of staples.
Figure 6:
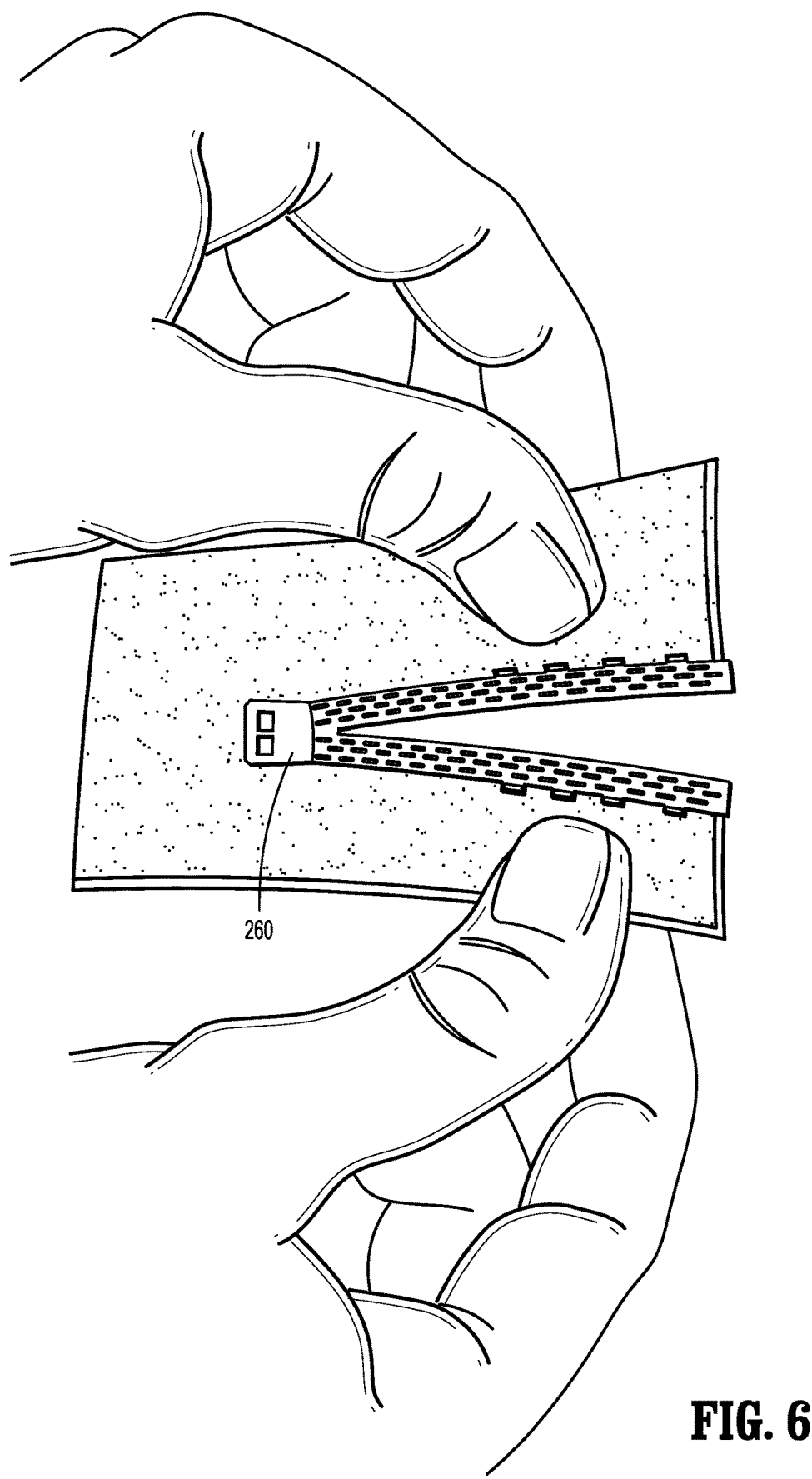
FIG. 6 is a top plan view of the buttress material attached to foam material by linear rows of staples, with the divided portions of the buttress material displaced laterally.

To remove the buttress material 202 from the stapling instrument 300 and carrier 204, a first portion 202a of the buttress is grasped and moved laterally, and a second portion 202b of the buttress is moved in a lateral, opposite direction from the first portion (see FIGS. 5 and 6). In this way, the buttress material slides off the stapler 300 and carrier 204. The carrier 204 can be removed with the stapling instrument 300, or it can be separately removed.

Figure 4:
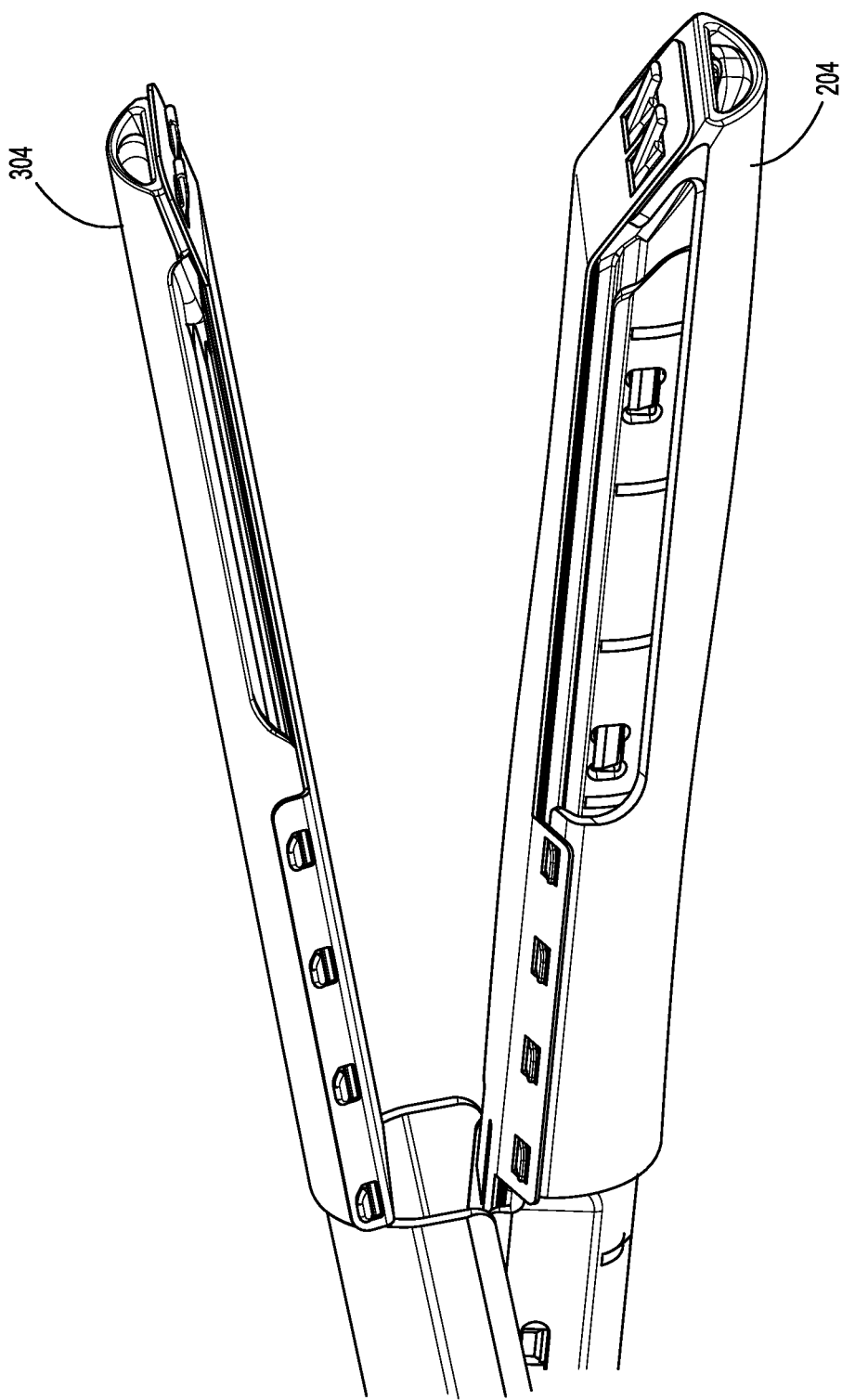
FIG. 4 is a perspective view of the buttress carrier assembly shown in FIG. 3 assembled with the jaws of an endoscopic stapling instrument.
Figure 7:
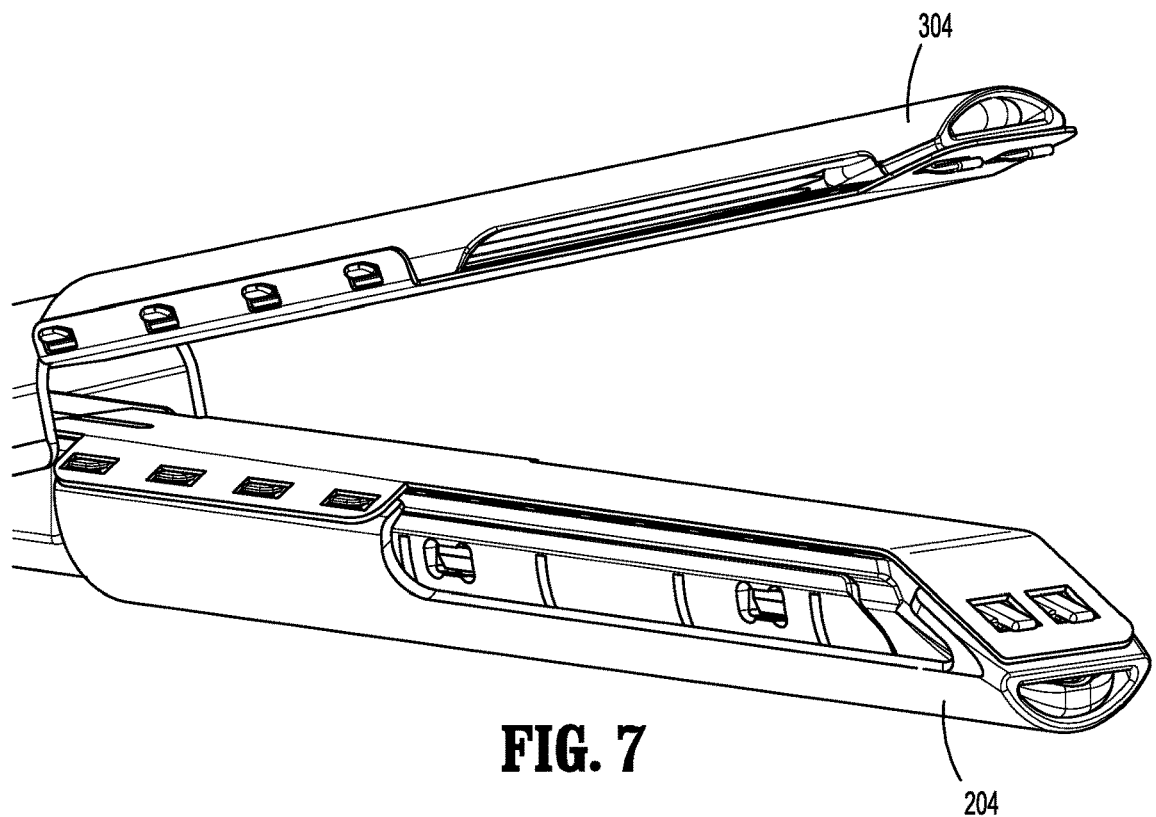
FIG. 7 is a perspective view of the buttress carrier assembly attached to each of the jaws of the endoscopic stapling instrument.
Figure 8:
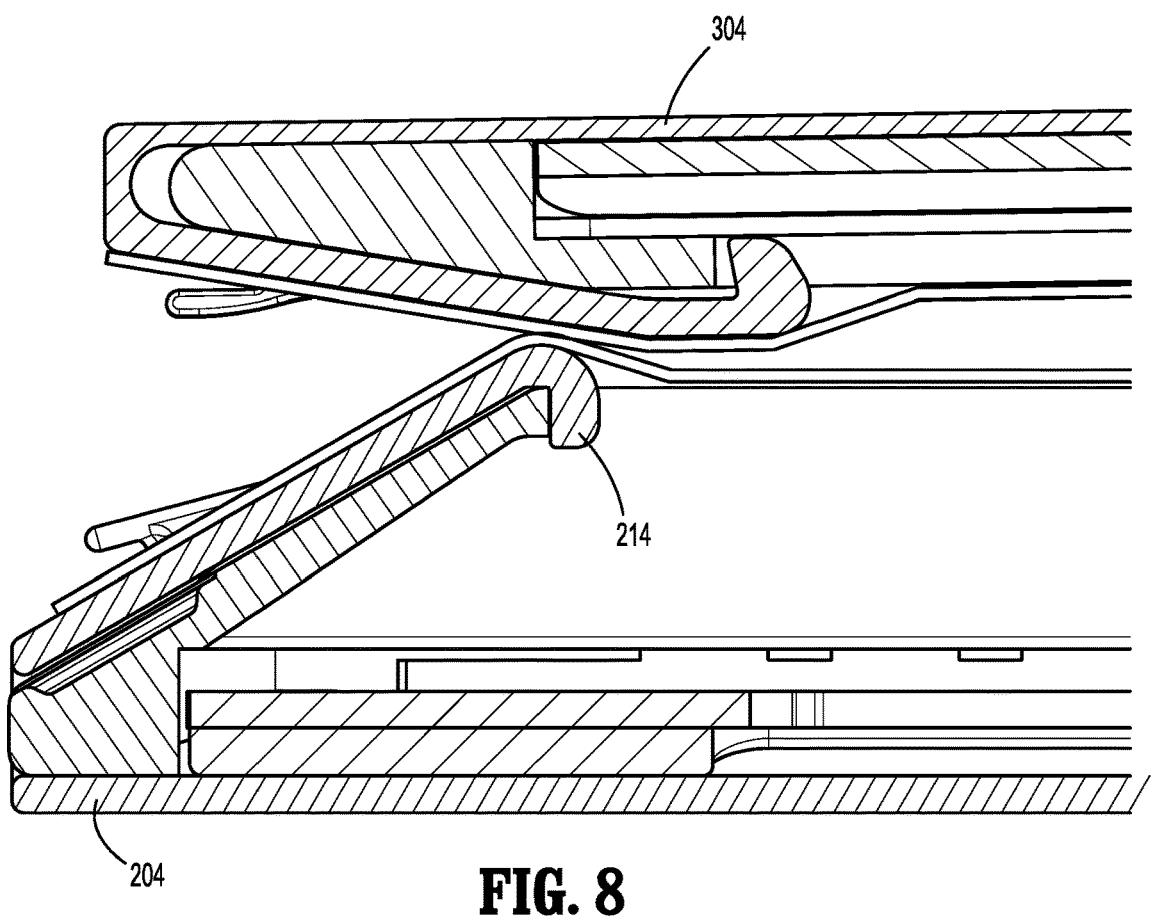
FIG. 8 is a cross-sectional view of the buttress carrier assembly and the distal end of the jaws of the endoscopic stapling instrument shown in FIG. 7.

In any of the embodiments disclosed herein, the carrier can be shaped to correspond to the particular jaw it is to be assembled with (see FIG. 4). In one example, a carrier 304 having a shape corresponding to the back of the anvil 306 and a carrier 204 corresponding to the back of the cartridge jaw. In FIGS. 7 and 8, the anvil has a lower profile and is more curved in shape than the cartridge jaw, which is deeper and may be rounded or more rectangular in shape. In further examples, the carrier 204 can include perforations for ease of removal from the instrument after use.

In FIG. 8, buttress carrier 204 is disposed on the cartridge jaw, whereas buttress carrier 304 is disposed on the anvil 50. Buttress carrier 204 has hook 214 engaging the knife slot 60a and buttress carrier 304 has hook 314 engaging knife slot 50a.

FIG. 4 shows buttress carrier assemblies on the staple cartridge jaw 304 and the anvil 306 jaw of the surgical stapler. In instruments having staple cartridge assemblies that are removable and replaceable, the staple cartridge assembly may have a buttress pre-loaded onto it, by the manufacturer. In these circumstances, the user can utilize a separately packaged buttress carrier assembly 200 that is ready for installation on the instrument's anvil. A surgical buttress material can be attached to the surgical stapling anvil using the buttress carrier assembly discussed above. In this way, the surgical stapling instrument can be re-used on the same patient, by reloading it with a staple cartridge assembly having a fresh set of staples ready to be fired and a fresh buttress material. The buttress carrier assembly is conveniently applied to the stapler anvil as discussed above.

The staple cartridge assembly, in any of the embodiments disclosed herein, houses surgical fasteners other than staples. Furthermore, staple cartridge assemblies having a buttress carrier assembly can be arranged for use with open stapling instruments, circular stapling instruments, or other types of instruments.

In any of the embodiments disclosed herein, the buttress carrier assembly 200 can include, or be used with sutures, straps with Velcro or other attachment features, adhesives, etc.

In any of the embodiments disclosed herein, the surgical buttress material 202 can include, or be used with, brachytherapy, chemotherapy, other medical materials or pharmaceuticals. The buttress materials can have pockets, apertures, or other features for retaining brachytherapy seeds with the buttress, or brachytherapy seeds or materials can be incorporated into a suture or sutures that are threaded into or through the buttress material or otherwise attached thereto. A coating having brachytherapy materials can be applied to a buttress material by spraying or dipping. Chemotherapy pharmaceuticals or agents can be incorporated into the material of the buttress, coated thereon, or applied as part of a suture or suture or other feature.

In general, linear staplers, including open and endoscopic devices, can have two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such an instrument is disclosed, for example, in U.S. Pat. No. 6,202,914, the entire content of which is incorporated herein by reference.

Some staplers apply a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. An example of such a stapler is disclosed in U.S. Pat. No. 5,065,929, the entire content of which is incorporated herein by reference.

Some of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,865,361, the entire content of which is incorporated herein by reference.

It is further contemplated that the surgical buttress may be configured for use with a circular stapling apparatus, or a semi-circular stapling apparatus. Surgical stapling devices for applying an annular array of staples or fasteners to tissue are well known in the art. These devices typically include means for controlling the spacing between the fastener assembly and the anvil member at the distal end of the apparatus. The fastener assembly generally includes a circular array of fasteners such as staples, while the anvil member includes means for completing the circular anastomosis, typically an array of bucket members that clinch the staples after the staples are expelled from the fastener assembly, or may include a locking member for the anastomosis ring. The means for advancing or retracting the anvil in relation to the fastener assembly typically includes a wing-nut type mechanism at a proximal end of the instrument or a rotatable knob member, both of which engage a worm gear arrangement in the handle mechanism to slowly, and methodically advance the anvil member towards the fastener assembly.

In use, the circular instrument is positioned within the lumen of an organ such as the stomach, esophagus, or intestine in order to perform the anastomosis. The tissue is positioned between the anvil and the fastener assembly and is typically tied off, for example, by a purse string suture. Thereafter, the anvil member is advanced towards the fastener assembly by rotation of the rotatable knob or wing nut assembly at the proximal end of the instrument to hold the tissue between the anvil member and the fastener assembly. As the staples or the fasteners are expelled from the fastener assembly, a circular knife typically follows the application of the staples to excise unwanted tissue at the anastomosis site. The instrument is then removed from the lumen of the organ.

Circular instruments are disclosed, for example, in U.S. Pat. No. 5,915,616, the entire contents of which is incorporated herein by reference.

In another U.S. Pat. No. 5,137,198 to Nobis et al. ("Nobis"), a fastener applying device including a cartridge that is advanced towards an anvil assembly by an advancing mechanism is disclosed. The advancing mechanism includes a first actuator member for advancing the cartridge towards the anvil assembly at an accelerated rate and a second actuator member spaced from the first actuator member for incrementally advancing the cartridge towards the anvil assembly. In another example of a surgical stapler, U.S. Pat. No. 5,964,394, the entire contents of which is incorporated herein by reference.

In a further embodiment, a buttress component 500 can be formed from a buttress material and can include an elongate member 502, a folded portion 504, and a buttress portion 506. The buttress portion 506 is attached to the folded portion and separated therefrom by perforation features 508. The elongate member 502 is long enough to extend the length of the endoscopic shaft 602 of an endoscopic stapler 600, and be accessible outside the patient's body. Alternatively or additionally, a suture is attached to the elongate member, or to the folded portion 504. When the folded portion is folded onto the buttress portion, a tubular shape 510 is formed. The tubular shape 510 is large enough, and shaped to facilitate, the reception of a stapler anvil 604, or staple cartridge jaw 606. When the elongate member 502 is pulled, the folded portion and elongate member are separated from the buttress portion. The perforation features can be omitted. The folded portion can be one or more sections of material, and can be made from the same material as the buttress material, or from a different material. The folded portion or portions can be welded, or adhesive can be used, to form the tubular shape. Alternatively, the buttress material can be similarly attached to the folded portion or portions, or to itself.

Figure 9:
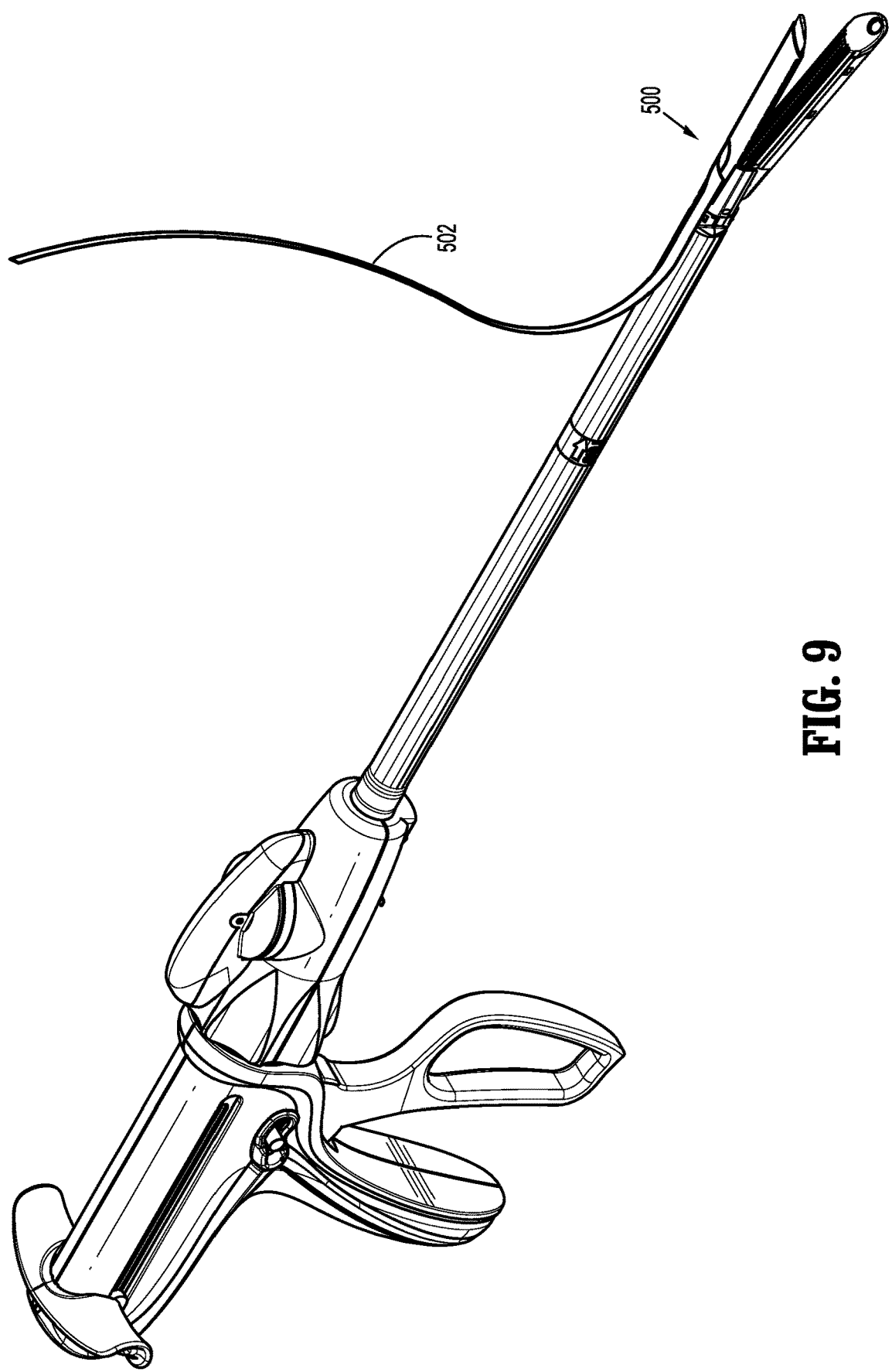
FIG. 9 is a perspective view of an endoscopic stapling instrument having a buttress component disposed thereon, in accordance with aspects of the present disclosure.

As can be seen from FIG. 9, the buttress component 500 is disposed on the anvil of an endoscopic stapling instrument. The folded portion 502 is disposed around the side 604a of the anvil that is opposite the tissue contacting side 604b. The elongate member 502 extends down the shaft 602 of the instrument and can terminate in a handle 602a or other graspable portion.

Figure 10:
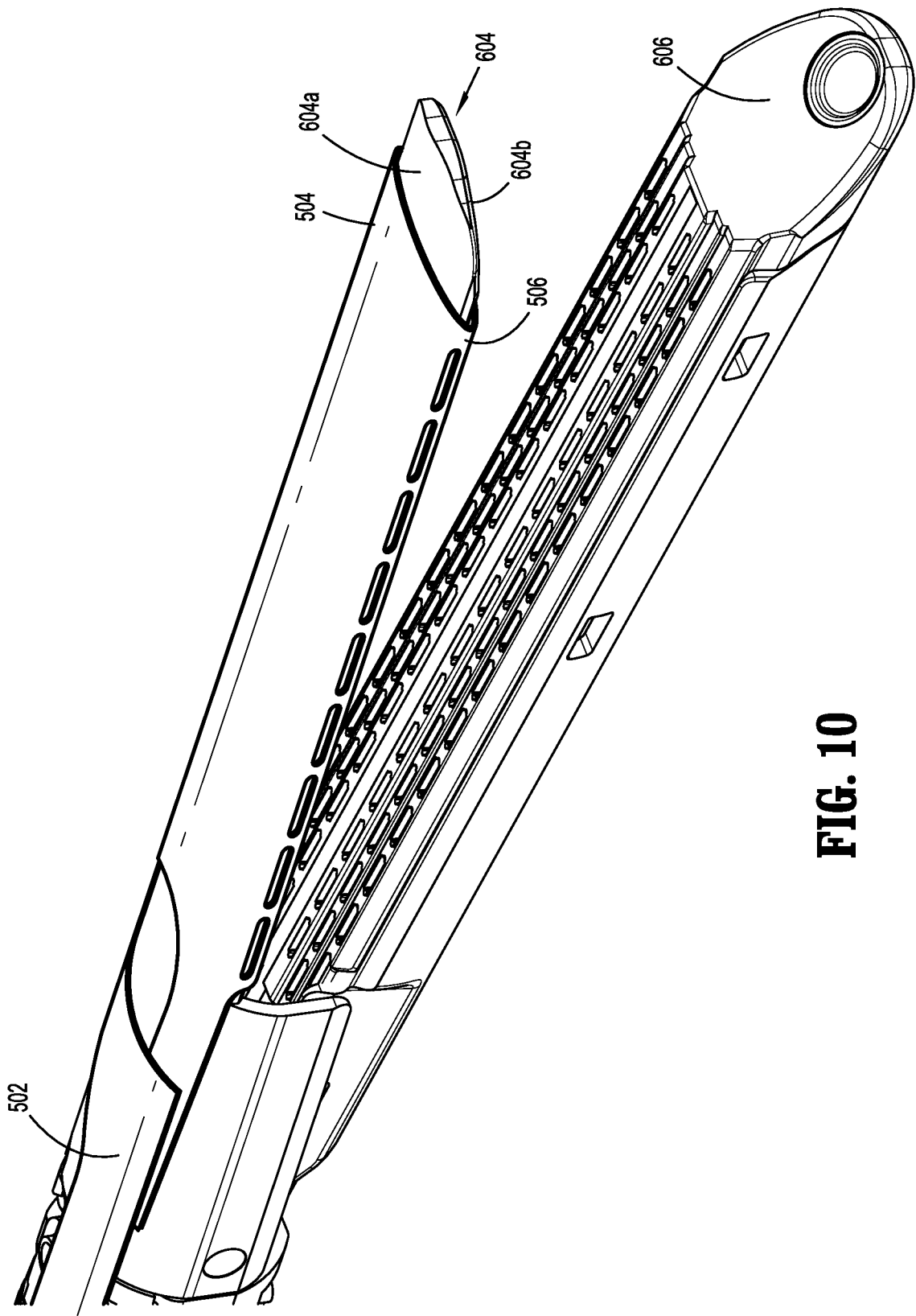
FIG. 10 is a perspective view of the end effector of the instrument of FIG. 9, showing the buttress component disposed thereon.

Perforation features 508 can be small pin-holes in the buttress material, larger openings 508a in the buttress material, or are formed by separate members attaching the buttress portion 506 to the folded portion 504. The perforation features 508 can be a single feature, such as a line of weakness in the material or materials. In FIG. 10, larger openings are shown, and the buttress material is a non-woven polyglycolide material, although other bio-compatible, bio-absorbable, wovens, non-wovens, meshes, polymers and co-polymers can be used. The openings can be formed using a laser, a cutting blade, or other methods. The material for the buttress material can be as discussed above. In one example, the component 500 is made from one sheet of non-woven polyglycolic acid and is laser-cut to form the features discussed herein.

Figure 11:
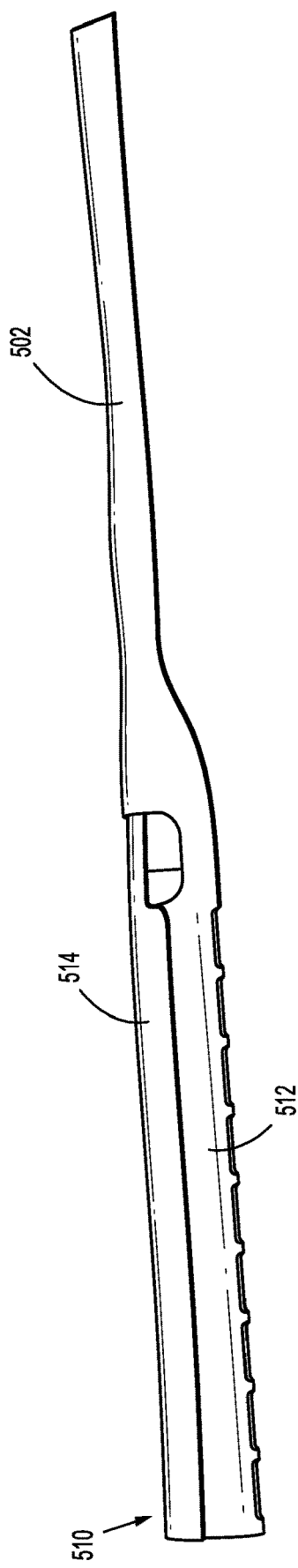
FIG. 11 is a perspective view of the buttress component of FIGS. 9 and 10, separate from the instrument.

The folded portion 504 can be welded to itself or to the buttress portion 506. As shown in FIG. 11, a first folded portion 512 is welded to a second folded portion 514, on either side of the buttress portion. The elongate member 502 can be unitary with the buttress portion, and/or the folded portion or portions. In FIG. 11, the elongate member 502 is attached to the folded portions by welding (at 513), and can be the same material as the folded portion or portions, and/or buttress portion 506.

Figure 12:
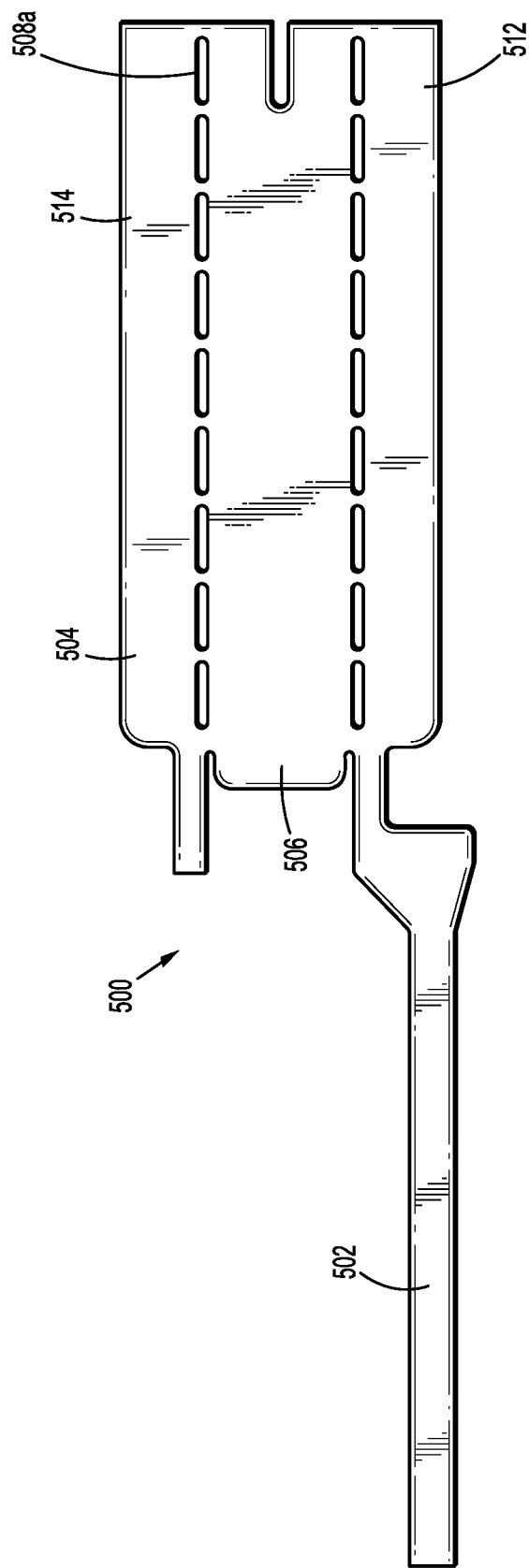
FIG. 12 is a plan view of the buttress component of FIGS. 9-11, in an unfolded condition.

The entire buttress component can be formed from a single sheet of material. As shown in FIG. 12, the starting material 520 is cut from a sheet, and the perforation features 508 are formed therein. The component 500 has a first folded portion 512, second folded portion 514, buttress portion 506, and elongate member 502. The folded portions 512, 514 can be folded before the component 500 is disposed on or around the anvil 604, or as the component 500 is applied to the anvil 604. The folded portion or portions, and the buttress portion can be attached to one another by welding, using adhesives, by tying with sutures, etc.

To remove the stapling instrument after the staples have been fired, the elongate member 502 is pulled, and the buttress portion is separated from the folded portions. The instrument, folded portion or portions, and elongate member can be removed from the surgical site together or separately. Thus, the buttress portion is stapled to tissue and the rest of the component tears away from the buttress portion.

Figure 13:
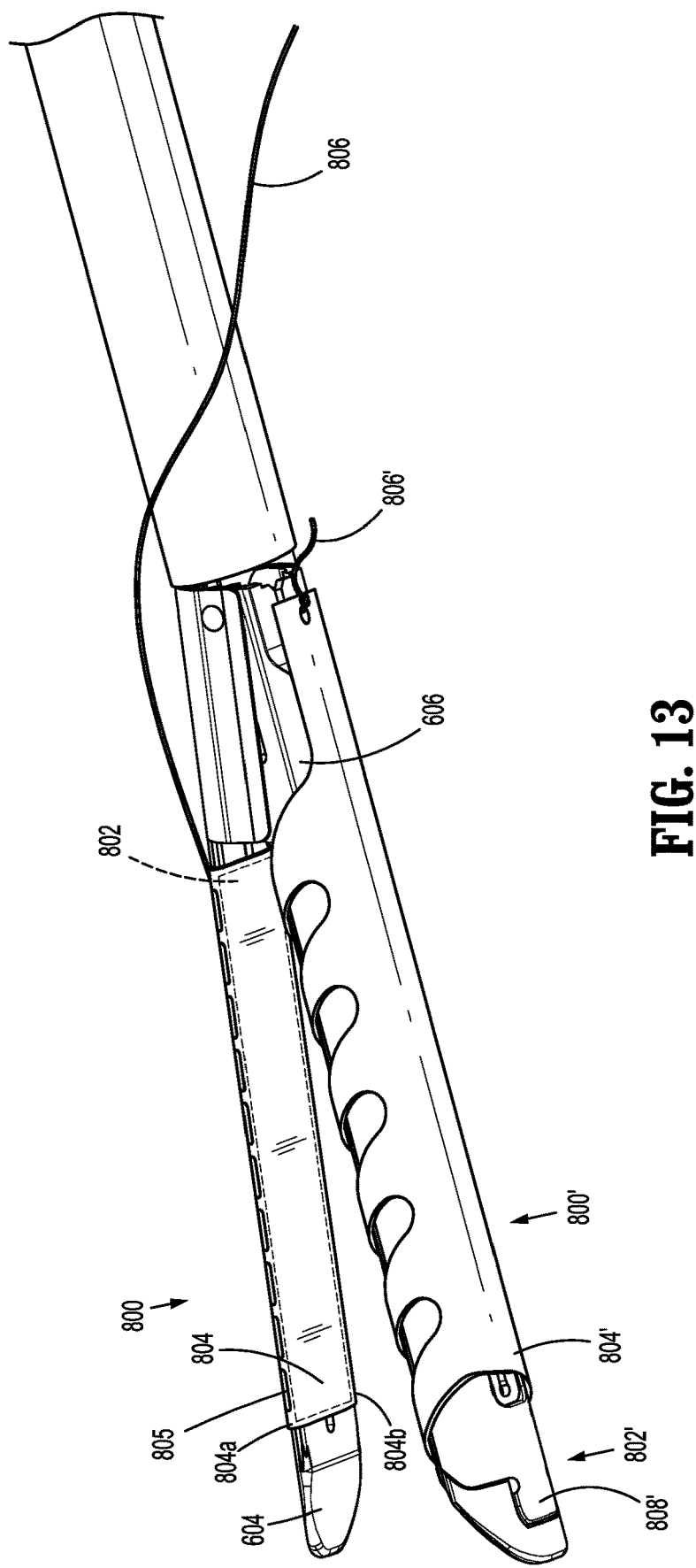
FIG. 13 is a perspective view of an end effector of an endoscopic surgical stapling instrument according to another aspect of the present disclosure, and having a buttress component disposed thereon.

In another embodiment of the present disclosure, as shown in FIG. 13, a buttress assembly 800 has a carrier 802 (shown in phantom), buttress material 804, and elongate member 806. The buttress assembly 800 is disposed on the stapler anvil 604. A buttress assembly 800', which also includes a carrier 802', buttress material 804', and elongate member 806', is disposed on the staple cartridge jaw 606. The elongate member 806 can be a suture, or can be an extension of the carrier 802 and integral therewith. The carrier 802 can be formed from a very thin sheet of material such as ABS (acrylonitrile butadiene styrene) plastic, mylar, polyester, or any bio-compatible material. The carrier 802 is preferably very thin, such as about 0.003 to about 0.008 thousandths of an inch. For example, the carrier 802 can be a thin, flexible sheet of polyester of about 0.006 thousandths of an inch in thickness.

The carrier 802 is formed with an elongate shape and flexibly conforming to the shape of the stapler anvil 604. The long sides of the carrier 802 have distally extending arms knot explicitly shown, but see e.g., distally extending arms 808' of the carrier 802') for directly engaging the buttress material 804. The buttress material 804 has sides 804a and 804b that extend upwardly from the tissue contacting surface of the anvil 604. The sides 804a and 804b can be separated from the rest of the buttress material 804 after the instrument is fired, and perforations or lines of weakness can be provided. The buttress material 804 has openings 805 on both sides of the buttress material 804 for receiving the arms of the carrier 802.

After the stapling instrument is fired, the elongate member 806 is pulled and the carrier 802 is separated from the buttress material 804. The buttress material and elongate member are removed from the surgical site. The shape of the arms, which have a hooked shape in the direction of the distal end of the stapler instrument end effector, can be relied on for retaining the buttress material, or some adhesive can be used. In addition, some adhesive can be used for retaining the buttress assembly 800 or buttress component 500 (FIG. 12) on the stapling instrument, or frictional forces can be relied on for retention. The elongate member 806 can be part of the carrier, or attached to the carrier, or a suture can be used.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Thus the scope of the embodiments should be determined by the appended claims and their legal equivalents, rather than by the examples given.

What is claimed is:

1. A surgical buttress component, comprising an elongate member, a folded portion and a buttress portion forming an elongate tube defining an opening therethrough for the reception of a selected one of an anvil stapler jaw or a cartridge stapler jaw, and a feature selected from the group consisting of a perforation, an elongate opening and a line of weakness disposed between and separating the buttress portion from the folded portion, the elongate member extending from the folded portion.

2. The surgical buttress component according to claim 1, wherein the buttress portion is formed from a buttress material.

3. The surgical buttress component according to claim 2, wherein the buttress material is selected from the group consisting of a woven, a non-woven, and a mesh.

4. The surgical buttress component according to claim 2, wherein the buttress material is formed from a bio-absorbable polymer.

5. The surgical buttress component according to claim 1, wherein the elongate member is sized to extend at least the length of an endoscopic shaft of an endoscopic stapler.

6. The surgical buttress component according to claim 1, wherein the elongate member is accessible outside the patient's body.

7. The surgical buttress component according to claim 1, wherein the elongate member is a suture attached to the folded portion.

8. The surgical buttress component according to claim 1, wherein the folded portion is more than one section of material.

9. The surgical buttress component according to claim 8, wherein the folded portion includes a first section and a second section, the first and second sections extending from opposed sides of the buttress portion and attached to one another.

10. The surgical buttress component according to claim 9, wherein the first and second sections of the folded portion are welded together.

11. The surgical buttress component according to claim 1, wherein the folded portion is made from a same material as the buttress portion.

12. The surgical buttress component according to claim 1, wherein the folded portion is made from a same sheet of material as the buttress portion, or the elongate member is made from the same sheet of material as the buttress portion, or both the folded portion and the elongate member is made from the same sheet of material as the buttress portion.

13. The surgical buttress component according to claim 1, wherein the folded portion is welded to form the elongate tube.

14. The surgical buttress component according to claim 1, wherein the folded portion is attached to the buttress portion.

15. The surgical buttress component according to claim 14, wherein the folded portion is attached to opposed sides of the buttress portion.

16. The surgical buttress component according to claim 1, wherein the elongate member extends from a proximal end of the folded portion.

17. The surgical buttress component according to claim 1, wherein the elongate member and the folded portion are integrally formed from a single material.

18. The surgical buttress component according to claim 17, wherein the buttress portion is integrally formed with the elongate member and the folded portion from the single material.

19. The surgical buttress component according to claim 1, wherein the feature extends linearly between the folded and buttress portions.

20. A surgical buttress component, comprising:
    an elongate member;
    a folded portion and a buttress portion forming an elongate tube defining an opening therethrough for the reception of a selected one of an anvil stapler jaw or a cartridge stapler jaw; and
    a feature selected from the group consisting of a perforation, an elongate opening and a line of weakness disposed between and separating the buttress portion from the folded portion, the feature extending linearly between the folded portion and the buttress portion.

* * * * *